(12) United States Patent
Hata et al.

(10) Patent No.: US 8,691,297 B2
(45) Date of Patent: Apr. 8, 2014

(54) ALCOHOLIC INJURY MITIGATING AGENT

(75) Inventors: Junichiro Hata, Tokyo (JP); Tomoko Tsuji, Tokyo (JP); Kenichi Yanagimoto, Tokyo (JP)

(73) Assignee: Nippon Suisan Kaisha, Ltd. (JP)

( * ) Notice: Subject to any disclaimer, the term of this patent is extended or adjusted under 35 U.S.C. 154(b) by 0 days.

(21) Appl. No.: 13/820,170

(22) PCT Filed: Sep. 1, 2011

(86) PCT No.: PCT/JP2011/069876
§ 371 (c)(1),
(2), (4) Date: Mar. 1, 2013

(87) PCT Pub. No.: WO2012/029898
PCT Pub. Date: Mar. 8, 2012

(65) Prior Publication Data
US 2013/0156861 A1    Jun. 20, 2013

(30) Foreign Application Priority Data

Sep. 1, 2010   (JP) .................................. 2010-195730

(51) Int. Cl.
*A01N 65/00*   (2009.01)

(52) U.S. Cl.
USPC ........................................................ 424/725

(58) Field of Classification Search
None
See application file for complete search history.

(56) References Cited

U.S. PATENT DOCUMENTS

2008/0274203 A1   11/2008   Bruheim et al.

FOREIGN PATENT DOCUMENTS

| EP | 2 332 424 A1 | 6/2011 |
|---|---|---|
| JP | 3197424 B2 | 10/1995 |
| JP | 11-276116 A | 10/1999 |
| JP | 2001-226277 A | 8/2001 |
| JP | 2002-161045 A | 6/2002 |
| JP | 2002-527604 A | 8/2002 |
| JP | 2004-534800 A | 11/2004 |
| WO | 00/23546 A1 | 4/2000 |
| WO | 02/102394 A2 | 12/2002 |
| WO | 2010/035749 A1 | 4/2010 |
| WO | 2010/035750 A1 | 4/2010 |
| WO | 2010/136900 A2 | 12/2010 |
| WO | 2010136900 A2 | 12/2010 |

OTHER PUBLICATIONS

International Preliminary Report on Patentability of International Application No. PCT/JP2011/069876, mailed Mar. 21, 2013.
Kouda, Takahiko, "Effects of polyunsaturated fatty acid (sun balance) and extract of oyster (dino balance) on blood ethanol and acetaldehyde concentration in human volunteers", Showa University School of Medicine, 1996, vol. 56, No. 6, pp. 591-600.
International Search Report for International Application No. PCT/JP2011/069876, mailed Sep. 27, 2011, with English translation.
Peil Ing-Peng, et al. "Protective Effects of a Staxanthin on acute alcohol liver injury in mice", Journal of Jiangsu University (Medicine Edition), vol. 18, No. 4, Jul. 2008, pp. 303-307 (see English Abstract).
Office Action for Chinese Patent Application No. 201180042380.X, dated Dec. 5, 2013; with partial English translation of the relevant portion.

*Primary Examiner* — Michael Meller
(74) *Attorney, Agent, or Firm* — Cantor Colburn LLP (57) ABSTRACT

The present invention relates to an alcoholic injury mitigating agent comprising krill oil as an active ingredient. The krill oil preferably comprises phospholipids in an amount of at least 30% by weight, ω3 polyunsaturated fatty acids in an amount of at least 5% by weight of the total fatty acids, eicosapentaenoic acid in an amount of at least 2% by weight of the total fatty acids, or docosahexaenoic acid in an amount of at least 1% by weight of the total fatty acids.

8 Claims, 5 Drawing Sheets

$\$\$$: p<0.01, vs. untreated group (Aspin-Welch test)
**: p<0.01, vs. ethanol + olive oil group (Aspin-Welch test)
: p<0.05, ##: p<0.01, vs. ethanol + olive oil group (Student-t test)

Fig. 3

$$: p<0.01, vs. untreated group (Aspin-Welch test)
**: p<0.01, vs. ethanol + olive oil group (Aspin-Welch test)
: p<0.01, vs. ethanol + olive oil group (Student-t test)

Fig. 4

&: p<0.05, &&: p<0.01, vs. untreated group (Aspin-Welch test)
**: p<0.01, vs. ethanol + olive oil group (Aspin-Welch test)
: p<0.01, vs. ethanol + olive oil group (Student-t test)

Fig. 5

&&: p<0.01, vs. untreated group (Aspin-Welch test)
: p<0.05, vs. ethanol + olive oil group (Student-t test)

Fig. 6

$: p<0.05, vs. untreated group (Aspin-Welch test)
: p<0.05, vs. ethanol + olive oil group (Student-t test)

Fig. 7

$$: p<0.01, vs. untreated group (Aspin-Welch test)
**: p<0.01, vs. ethanol + olive oil group (Aspin-Welch test)
: p<0.05, vs. ethanol + olive oil group (Student-t test)

Fig. 8

Mean ± SE    Wilcoxon signed rank test

ALCOHOLIC INJURY MITIGATING AGENT

CROSS REFERENCE TO RELATED APPLICATIONS

This is a U.S. national stage of application No. PCT/JP2011/069876, filed on 1 Sep. 2011. Priority under 35 U.S.C. §119(a) and 35 U.S.C. §365(b) is claimed from Japanese Application No. 2010-195730, filed 1 Sep. 2010, the disclosure of which is also incorporated herein by reference.

TECHNICAL FIELD

The present invention relates to agents for mitigating injuries caused by alcohol consumption such as drunken sickness and hangover, and injuries to the liver, blood, blood sugar and the like, as well as alcohol metabolism promoting agents.

BACKGROUND ART

Alcoholic beverages such as beer, wine, whiskey, rice wine and shochu have been enjoyed by people since long ago. A wide variety of alcoholic beverages have actually been produced and sold, contributing to people's rich dietary life.

While having such an aspect of enjoying people, alcoholic beverages may produce undesirable symptoms. Excessive drinking may cause drunken sickness or hangover where the symptoms of drunkenness (such as headache, dizziness, nausea, dehydration) persist on and/or after the following day of drinking. Further, excessive drinking for a long time may develop symptoms such as gout and liver dysfunction. Such alcohol-induced symptoms are common in that they are attributed to an increase in blood alcohol concentration caused by drinking.

There are several known inventions intended for promotion of alcoholic metabolism after drinking. For example, Japanese Unexamined Patent Application Publication No. 11-276116 discloses an alcohol metabolism promoting agent comprising a processed pork product prepared from pork treated with a protease (Patent Document 1). Japanese Unexamined Patent Application Publication No. 2002-161045 discloses an alcohol metabolism ameliorant comprising a fermented rice bran and soybean extract (Patent Document 2). Japanese Unexamined Patent Application Publication No. 2001-226277 discloses an alcohol absorption and metabolism regulating agent comprising a processed soybean product as an active ingredient (Patent Document 3).

CITATION LIST

Patent Documents

[Patent Document 1] Japanese Unexamined Patent Application Publication No. 11-276116
[Patent Document 2] Japanese Unexamined Patent Application Publication No. 2002-161045
[Patent Document 3] Japanese Unexamined Patent Application Publication No. 2001-226277

SUMMARY OF INVENTION

Technical Problem

An object of the present invention is to provide a pharmaceutical preparation, supplement, food, and the like that can mitigate injuries caused by alcohol consumption such as drunken sickness and hangover, and injuries to the liver, blood, blood sugar and the like, or an alcohol metabolism promoting agent, each of which comprises safe ingredients in an easy-to-consume form.

Solution to Problem

In the process of studying krill oil, the present inventors have found that krill oil has unexpected effects on alcohol metabolism, and completed the present invention.

The present invention provides the following alcoholic injury mitigating agent, and the following food and beverage comprising the same:

(1) An alcoholic injury mitigating agent comprising krill oil as an active ingredient;
(2) The alcoholic injury mitigating agent according to (1), wherein the mitigation of alcoholic injury is suppression of an increase in blood ethanol concentration, mitigation of a symptom of drunkenness, promotion of recovery from the symptoms of drunkenness, suppression of liver injury, suppression of dehydration, or suppression of an increase in blood glucose level;
(3) The alcoholic injury mitigating agent according to (1) or (2), wherein the mitigation of alcoholic injury is based on suppression of alcohol absorption and/or promotion of alcohol metabolism, each induced by the krill oil;
(4) The alcoholic injury mitigating agent according to any one of (1) to (3), wherein the krill oil comprises phospholipids in an amount of at least 25% by weight;
(5) The alcoholic injury mitigating agent according to any one of (1) to (4), wherein at least 5% by weight of the total fatty acids in the krill oil is ω3 polyunsaturated fatty acids;
(6) The alcoholic injury mitigating agent according to any one of (1) to (5), wherein at least 2% by weight of the total fatty acids in the krill oil is eicosapentaenoic acid;
(7) The alcoholic injury mitigating agent according to any one of (1) to (6), wherein at least 1% by weight of the total fatty acids in the krill oil is docosahexaenoic acid;
(8) The alcoholic injury mitigating agent according to any one of (1) to (7), wherein the daily consumption amount of the krill oil is in the range of 1 to 20000 mg;
(9) A food and beverage for ingesting the alcoholic injury mitigating agent according to any one of (1) to (8); and
(10) The food and beverage according to (9), wherein the krill oil is ingested in an amount of 1-20000 mg per a single dose.

In another aspect, the present invention provides, but is not limited to, the alcohol metabolism promoting agent as set forth below in (11) to (16):

(11) An alcohol metabolism promoting agent comprising krill oil;
(12) The alcohol metabolism promoting agent according to (11), wherein the krill oil is extracted from a krill-derived starting material using an organic solvent;
(13) The alcohol metabolism promoting agent according to (11) or (12), wherein the krill oil is extracted from a krill-derived starting material using ethanol;
(14) The alcohol metabolism promoting agent according to any one of (11) to (13), wherein the krill oil comprises phospholipids in an amount of at least 25% by weight;
(15) The alcohol metabolism promoting agent according to any one of (11) to (14), wherein ω3 polyunsaturated fatty acids accounts for at least 5% by weight of the total fatty acids in the krill oil; and
(16) The alcohol metabolism promoting agent according to any one of (11) to (15), wherein the krill oil contains astaxanthin in an amount of at least 100 ppm.

Further, the present invention provides the following methods:

A method for promoting alcohol metabolism, comprising administering an alcohol metabolism promoting agent comprising krill oil; and A method for preventing or ameliorating alcoholic liver injury, tissue injury associated with dehydration, or a disease caused by an increase in blood glucose level, the method comprising administering an alcohol metabolism promoting agent comprising krill oil.

BRIEF DESCRIPTION OF DRAWINGS

FIG. 4 shows the changes in hematocrit (HCT) according to Example 2. The bars in the graph show, in the order from left to right, the values for the untreated group (A1), the 60% (v/v) ethanol+olive oil group (A2), the 60% (v/v) ethanol+krill oil (200 mg/kg) group (A3), and the 60% (v/v) ethanol+krill oil (1,000 mg/kg) group (A4). The data in the figure are expressed as averages. & represents $p<0.05$, vs. untreated group (Student-t test); && represents $p<0.01$, vs. untreated group (Student-t test); ** represents $p<0.01$, vs. ethanol+olive oil group (Aspin-Welch test); and ## represents $p<0.01$, vs. ethanol+olive oil group (Student-t test).

FIG. 5 shows the changes in blood aspartate aminotransferase (AST) activity (IU/L) in the rats after oral alcohol administration according to Example 2. This enzyme activity is found in the liver, so the AST activity in the blood serves as an indicator of liver injury. The bars in the graph show, in the order from left to right, the values for the untreated group (A1), the 60% (v/v) ethanol+olive oil group (A2), the 60% (v/v) ethanol+krill oil (200 mg/kg) group (A3), and the 60% (v/v) ethanol+krill oil (1,000 mg/kg) group (A4). The data in the figure are expressed as averages. $$ represents $p<0.01$, vs. untreated group (Asp in-Welch test); and # represents $p<0.05$, vs. ethanol+olive oil group (Student-t test).

FIG. 6 shows the changes in blood alanine aminotransferase (ALT) activity (IU/L) in the rats after oral alcohol administration according to Example 2. This enzyme is found in the liver, so the ALT activity in the blood serves as an indicator of liver injury. The bars in the graph show, in the order from left to right, the values for the untreated group (A1), the 60% (v/v) ethanol+olive oil group (A2), the 60% (v/v) ethanol+krill oil (200 mg/kg) group (A3), and the 60% (v/v) ethanol+krill oil (1,000 mg/kg) group (A4). The data in the figure are expressed as averages. $ represents $p<0.05$, vs. untreated group (Asp in-Welch test); and # represents $p<0.05$, vs. ethanol+olive oil group (Student-t test).

FIG. 7 shows the changes in blood glucose level in the rats according to Example 2. The bars in the graph show, in the order from left to right, the values for the untreated group (A1), the 60% (v/v) ethanol+olive oil group (A2), the 60% (v/v) ethanol+krill oil (200 mg/kg) group (A3), and the 60% (v/v) ethanol+krill oil (1,000 mg/kg) group (A4). The data in the figure are expressed as averages. $$ represents $p<0.01$, vs. untreated group (Asp in-Welch test); ** represents $p<0.01$, vs. ethanol+olive oil group (Aspin-Welch test); and # represents $p<0.05$, vs. ethanol+olive oil group (Student-t test).

DESCRIPTION OF EMBODIMENTS

The present invention will be more specifically described below.

As used herein, "krill" may be any arthropod that belongs to, subclass Malacostraca, class Crustacea, phylum Arthropoda, and includes arthropods that belong to order Euphausiacea, superorder Eucarida, subclass Malacostraca, class Crustacea, phylum Arthropoda, such as Antarctic krill (*Euphausia superba*), and arthropods that belong to order Mysida, superorder Peracarida, subclass Malacostraca, class Crustacea, phylum Arthropoda, such as mysids caught in the oceans near Japan.

As used herein, "krill oil" refers to the oil obtained from the krill described above.

The krill oil is characterized in that it has high phospholipids content. Phospholipid is known as a major constituent of the cell membrane and refers to a substance that has a hydrophilic phosphate moiety and a hydrophobic fatty acid moiety. Phospholipids are divided into glycerophospholipids and sphingophospholipids by the difference in their skeletal structure. As referred to herein, phospholipids include both types of phospholipids, with glycerophospholipids being preferred. Glycerophospholipids include, but are not limited to, phosphatidyl choline, phosphatidyl ethanolamine, phosphatidyl serine, phosphatidylinositol, phosphatidylglycerol, cardiolipin, and phosphatidic acid, and mixtures of two or more thereof. In the present invention, at least phosphatidyl choline is preferably contained as phospholipids. The phospholipids content in the krill oil is, for example, 5-80% by weight and particularly preferably 30-60% by weight. Alternatively, the krill oil can contain phospholipids in an amount of preferably at least 25% by weight and more preferably at least 35% by weight.

The krill oil is also characterized in that it contains ω3 polyunsaturated fatty acids. As used herein, "ω3 polyunsaturated fatty acids" means fatty acids having 18 or more carbons and 3 or more double bonds or preferably 5 or more double bonds, in which the third and fourth carbons from the terminal carbon opposite to the carboxyl side of the fatty acid molecule are joined by a double bond. Such fatty acids include, but are not limited to, α-linolenic acid (18:3), eicosapentaenoic acid (20:5), docosapentaenoic acid (22:5), and docosahexaenoic acid (22:6). ω3 polyunsaturated fatty acids may be present in a free state or in the form of lipids involving ester bonds. The proportion of ω3 polyunsaturated fatty acids in the total fatty acids present in the krill oil is, for example, 5-60% by weight, preferably 10-50% by weight and more preferably 10-30% by weight. It is preferred for the purpose of the present invention that the proportion of ω3 polyunsaturated fatty acids in the total fatty acids be contained in an amount of at least 5% by weight, more preferably at least 10% by weight and still more preferably at least 15% by weight. It is particularly preferred that eicosapentaenoic acid be contained in an amount of at least 2% by weight and preferably at least 10% by weight, and/or that docosahexaenoic acid be contained in an amount of at least 1% by weight and preferably at least 3% by weight.

The krill oil may further contain astaxanthin. Astaxanthin, a compound that belongs to the carotenoid family, is generally found in shellfish such as crab and shrimp. Astaxanthin may be present in a free state or in the form of lipids involving ester bonds, and is contained in the krill oil in an amount of, for example, 20-1,000 ppm, preferably 50-600 ppm, more preferably 50-500 ppm, still more preferably 100-400 ppm, and particularly preferably 100-250 ppm.

As long as having the above-mentioned properties, the krill oil used in the present invention may be prepared by any methods—for example, it can be prepared with reference to known methods as typically disclosed in WO 2010/035749 A1 and WO 2010/035750 A1. The krill oil can be obtained by, for example, extracting it from solids as a krill-derived starting material using a suitable organic solvent. The suitable organic solvent is one or a combination of two or more of, for example, alcohols such as methanol, ethanol, propanol, isopropanol, butanol, propyleneglycol and butylene glycol; methyl acetate, ethyl acetate, acetone, chloroform, toluene, pentane, hexane, and cyclohexane, with ethanol or a hexane-ethanol mixture being preferred. In the process of extraction, the solvent mixing ratio or the starting material/solvent ratio may be designed as desired.

The foregoing solids as a krill-derived starting material can be obtained by, for example, squeezing the whole or a part of the krill to give a squeezed liquid and heating the resulting squeezed liquid to separate solids and water-soluble components. Instead of obtaining the squeezed liquid, the whole or a part of the krill may be directly subjected to heat coagulation to give solids.

The squeezing can be performed using a commonly used apparatus such as a hydraulic squeezer, a screw press, a meat separator, a press dehydrator, a centrifuge, or a combination thereof The squeezed liquid may be heated under atmospheric pressure, pressurized, or reduced pressure conditions at a temperature of 50° C. or higher, preferably 70-150° C. and particularly preferably 85-110° C. The heating is performed to separate solids and water-soluble components, and filtration, centrifugation, or other treatments are performed to give the solids.

The present invention provides an alcoholic injury mitigating agent comprising krill oil as an active ingredient. The alcoholic injury mitigating agent can be used for mitigating injuries caused by alcohol consumption, and this effect is based on the alcohol absorption inhibition action and/or alcohol metabolism promotion action of the krill oil. Therefore, the present invention also provides an alcohol metabolism promoting agent comprising krill oil. As referred to herein, the mitigation of alcoholic injury includes, but is limited to, suppression of an increase in blood ethanol concentration, mitigation of a symptom of drunkenness, promotion of recovery from the symptoms of drunkenness, suppression of liver injury, suppression of dehydration, or suppression of an increase in blood glucose level.

The alcoholic injury mitigating agent and alcohol metabolism promoting agent of the present invention preferably use the krill oil extracted as described above but may use a product containing the krill oil, such as ground, shelled, or dried krill.

The alcoholic injury mitigating agent and alcohol metabolism promoting agent comprise an effective amount of the krill oil. As referred to herein, the effective amount may be any amount that is effective either for mitigating injuries caused by alcohol consumption or for promoting alcohol metabolism, for example, such an amount that allows a rat to consume the krill oil at a concentration of 10-5,000 mg/kg and preferably 100-2,000 mg/kg daily. The daily effective amount for a human is preferably 1-5,000 mg/kg and particularly preferably 10-2,000 mg/kg, and more specifically, it is preferred to prepare such a capsule or supplement that enables consumption of 1-500 mg/kg, preferably 1-200 mg/kg and more preferably 1-100 mg/kg daily. Such an amount may be consumed once daily or in two, three or more divided doses. As illustrated in Examples, the alcoholic injury mitigating agent and alcohol metabolism promoting agent of the present invention take effect even if it is consumed 30 minutes before alcohol consumption, and therefore also preferred are such usages as taking it in an amount of 1-20000 mg and preferably 100-5000 mg before alcohol consumption to prevent hangover or the like.

The inventive alcoholic injury mitigating agent and alcohol metabolism promoting agent comprising krill oil are effective for reducing blood alcohol concentration and also for reducing the occurrence of acetaldehyde.

The present invention provides a method for preventing or ameliorating drunken sickness or hangover, comprising: administering the alcoholic injury mitigating agent or alcohol metabolism promoting agent comprising krill oil to an animal such as a human. Excessive alcohol consumption causes symptoms such as headache, nausea, drunkenness, dizziness, malaise, and anorexia. The possible factors associated with these symptoms include dehydration caused by alcohol. The alcoholic injury mitigating agent and alcohol metabolism promoting agent of the present invention are effective for reducing blood alcohol concentration and therefore is suitable for the above-mentioned purposes.

The present invention provides a method for preventing or treating a symptom or disease caused by an increase in blood glucose level, comprising: administering the alcoholic injury mitigating agent or alcohol metabolism promoting agent comprising krill oil to an animal such as a human. As referred to herein, the symptom caused by an increase in blood glucose level includes, but is not limited to, malais, thirst, polyuria, hunger sensation, and weight gain. The disease caused by an increase in blood glucose level includes, but is not limited to, complications associated with arteriosclerosis. The alcoholic injury mitigating agent and alcohol metabolism promoting agent of the present invention are effective for preventing an increase in blood glucose level associated with alcohol consumption and therefore are suitable for the above-mentioned purposes.

The present invention provides a method for preventing or treating alcoholic liver injury, comprising: administering the alcoholic injury mitigating agent or alcohol metabolism promoting agent comprising krill oil to an animal such as a human. As referred to herein, the alcoholic liver injury refers to a disease caused by excessive alcohol consumption for a long time. The alcoholic liver injury includes, but is not limited to, chronic hepatitides such as alcoholic fatty liver, alcoholic hepatic fibrosis, and alcoholic cirrhosis, and acute hepatitides such as alcoholic hepatitis.

The alcoholic fatty liver is an early stage of alcoholic liver injury, where decreased liver lipolysis function causes accumulation of neutral fats in the liver, leading to the development of fatty liver. The alcoholic hepatic fibrosis means a severe alcoholic fatty liver where necrosis of hepatocytes and fibrosis of the tissues surrounding the necrotic area develop. The alcoholic cirrhosis means a severe alcoholic hepatic fibrosis where advanced chronic hepatitis causes severe disruption of hepatocytes, bringing the entire liver into the state of being covered with fiber. The alcoholic hepatitis is a disease where hepatocytes are severely damaged.

Such alcoholic liver injuries are caused by damage to hepatocytes by alcohol. The alcoholic injury mitigating agent and alcohol metabolism promoting agent of the present invention are capable of protecting hepatocytes and preventing them from being damaged and therefore are suitable for the above-mentioned purposes.

The mitigation effects for injuries caused by alcohol consumption or the alcohol metabolism promotion effect can be evaluated on the basis of the results of, for example, (1) blood ethanol concentration, (2) observation of general condition, (3) hematocrit (HCT), (4) blood aspartate aminotransferase (AST) activity, (5) blood alanine aminotransferase (ALT), (6) blood glucose level, (7) breath ethanol concentration, and (8) breath acetaldehyde concentration. In the present specification, the above-noted parameters were measured by the following procedures, unless otherwise specified.

(1) Blood ethanol concentration: This parameter makes it possible to identify the change in the concentration of alcohol remaining in the body after alcohol consumption. If alcohol metabolism is promoted, the blood ethanol concentration decreases and recovers faster to its normal level. The blood ethanol concentration can be measured by ultraviolet spectrophotometry using F-Kit Ethanol (J. K. International Inc.).

(2) Observation of general condition: The drunkenness caused by alcohol administration is evaluated as a score by observing body posture, mobility and righting reflex. If alcohol metabolism is promoted, the degree of drunkenness is mitigated and the general condition recovers faster to its normal state. The general condition can be evaluated on the basis of the following criterion:

0 point: The body posture, mobility and righting reflex are all normal;

1 point: Limbs cannot be kept in balance but walking is possible and the righting reflex is normal (slight drunkenness);

2 points: Limbs cannot be kept in balance and walking is impossible but the righting reflex is normal (inebriation and somnolence); and 3 points: Limbs cannot be kept in balance, walking is impossible, and the righting reflex is lost (dead drunkenness and coma).

(3) Hematocrit (HCT): This parameter represents the percentage of hemocytes in the whole blood. When alcohol is consumed, antidiuretic hormone secretion is reduced to thereby promote diuresis, so that the water content in the body decreases. As a result, the plasma volume decreases and the amount of hemocytes in the whole blood relatively increases, causing an increase in HCT. In other words, the hematocrit represents the percentage by volume of hemocytes in the blood, and an increase in this value reflects a decrease in the percentage of water in the blood. HCT can be used as an indicator of dehydration caused by alcohol consumption. If alcohol metabolism is promoted, dehydration is resolved and thus HCT decreases. HCT can be measured by sheath flow DC detection using a multi-parameter automated hematology analyzer (XT-2000i, Sysmex Corporation).

(4) Blood aspartate aminotransferase (AST) activity: AST catalyzes the reaction for generating glutamic acid and oxaloacetic acid from aspartic acid and 2-oxoglutaric acid. AST is present in hepatocytes, red blood cells, cardiac muscle, skeletal muscles and elsewhere, and leaks out into the blood due to necrocytosis or other factors. Therefore, measuring the AST activity in the blood makes it possible to determine the degree of liver injury induced by alcohol consumption. The AST activity can be measured by the JSCC standardization-compliant method using an automatic analyzer (Type 7170, Hitachi, Ltd.).

(5) Blood alanine aminotransferase (ALT) activity: ALT catalyzes the reaction for converting pyruvic acid and glutamic acid into alanine and α-ketoglutaric acid. ALT is mainly present in the liver and leaks out into the blood due to necrosis of hepatocytes or other factors. Therefore, measuring the ALT activity in the blood makes it possible to determine the degree of livery injury induced by alcohol consumption. The ALT activity can be measured by the JSCC standardization-compliant method using an automatic analyzer (Type 7170, Hitachi, Ltd.).

(6) Blood glucose level: Alcohol consumed by drinking or other activities is oxidized into acetaldehyde by alcohol dehydrogenase (ADH). This reaction involves reduction of $NAD^+$ to NADH and thus produces a shortage of $NAD^+$ required in glycolysis, so that glucose degradation through glycolysis is inhibited. However, increased NADH concentration exasperates gluconeogenesis, leading to an increase in blood glucose level. Therefore, measuring the blood glucose level makes it possible to determine the degrees of inhibition of glucose degradation and state of increased gluconeogenesis which are caused by alcohol consumption. The blood glucose level can be measured by the Hexokinase/G6-PDH (hexokinase/glucose-6-phosphate dehydrogenase) method using an automatic analyzer (Type 7170, Hitachi, Ltd.).

(7) Breath ethanol concentration: The concentration of ethanol contained in breath has a correspondence with the blood ethanol concentration. Therefore, measuring the breath ethanol concentration makes it possible to identify the change in blood ethanol concentration. The breath ethanol concentration can be measured by passing breath through an ethanol detector tube (Gastec Corporation, No. 112L) connected to a detector (Gastec Corporation, GV-100S) for about 4 minutes. The tube has a color change zone, in which the length of the portion of this zone that changes in color from light red to light blue indicates an ethanol concentration by a scale on the tube, and resulting value of ethanol concentration is corrected for the effect of temperature to give a measured value.

(8) Breath acetaldehyde concentration: Acetaldehyde is a causative agent of uncomfortable feeling and alcoholic liver injury induced by alcohol consumption. The breath acetaldehyde concentration has a correspondence with a blood acetaldehyde concentration. Therefore, measuring the breath acetaldehyde concentration makes it possible to identify the change in blood acetaldehyde concentration. The concentration of acetaldehyde contained in breath can be measured by passing breath through an ethanol detector tube (Gastec Corporation, No. 92L) connected to a detector (Gastec Corporation, GV-100S) for about 2 minutes. The tube has a color change zone where the length of the portion of this zone that changes in color from light red to light blue indicates an ethanol concentration, by a scale on the tube, and resulting value of ethanol concentration is corrected for the effect of temperature to give a measured value.

The components of the krill oil can be analyzed as described below. Unless otherwise specified, the analysis data shown in the present specification were obtained according to the procedures described above.

The phospholipids content can be measured by, for example, dissolving 300 mg of krill oil in hexane, subjecting the resulting solution to silica gel chromatography, eluting and collecting the adsorbed fractions using chloroform, vacuum distilling the solvent, and measuring the weight of the residue.

The fatty acids composition can be analyzed by methyl esterifying constituent fatty acids in the presence of boron trifluoride and then subjecting them to gas chromatography. The fatty acids composition can be determined by calculating the percentage that the peak area derived from each of the constituent fatty acids accounts for in the total peak area derived from the total fatty acids. The conditions for gas chromatographic analysis can be designed as described below.

Analyzer: 6890N Network GC System (Agilent Technologies);

Column: DB-WAX (column length: 30 m, internal diameter: 250 μm, thickness: 0.27 μm, model No.: 122-7032, J&W Scientific);

Column temperature: Raised from 180° C. to 230° C. at a rate of 30° C./min and then hold at 230° C. for 15 minutes;

Inlet temperature: 250° C.;

Detector temperature: 250° C.;

Detector: FID;

Carrier gas: Helium.

The astaxanthin content was measured according to the method disclosed by Jacobs P. B., et al. (*Comp. Biochem. Physiol.*, 72B, 157-160, 1981). Free astaxanthin was prepared from an esterified product by an esterase enzyme, and the total astaxanthin amount was quantified by HPLC on the basis of the authentic sample.

The alcoholic injury mitigating agent and alcohol metabolism promoting agent of the present invention may optionally contain known components such as coloring agents, preservatives, flavors, flavoring agents, coating agents, antioxidants, vitamins, amino acids, peptides, proteins, and minerals (e.g., iron, zinc, magnesium, iodine).

Examples of antioxidants includes dried yeast, glutathione, lipoic acid, quercetin, catechins, coenzyme Q10, enzogenol, proanthocyanidins, anthocyanidin, anthocyanin, carotenes, lycopene, flavonoid, resveratrol, isoflavones, zinc, melatonin, ginkgo biloba leaf, *Alpinia zerumbet* leaf, hibiscus, or extracts thereof Examples of vitamins include vitamin A group (for example, retinal, retinol, retinoic acid, carotene, dehydroretinal, lycopene, and salts thereof), vitamin B group (for example, thiamine, thiamine disulfide, dicethiamine, octothiamine, cycotiamine, bisibuthiamine, bisbentiamine, prosultiamine, benfotiamine, fursultiamine, riboflavin, flavin adenine dinucleotide, pyridoxine, pyridoxal, hydroxocobalamin, cyanocobalamin, methylcobalamin, deoxyadenosylcobalamin, folic acid, tetrahydrofolic acid, dihydrofolic acid, nicotinic acid, nicotinic acid amide, nicotinic alcohol, pantothenic acid, panthenol, biotin, choline, inositol, pangamic acid, and salts thereof), vitamin C group (ascorbic acid and derivatives thereof, erythorbic acid and derivatives thereof, and pharmacologically acceptable salts thereof), vitamin D group (for example, ergocalciferol, cholecalciferol, hydroxycholecalciferol, dihydroxycholecalciferol, dihydrotachysterol, and pharmacologically acceptable salts thereof), vitamin E group (for example, tocopherol and derivatives thereof, ubiquinone derivatives and pharmacologically acceptable salts thereof), and other vitamins (for example, carnitine, ferulic acid, y-oryzanol, orotic acid, rutin (vitamin P), eriocitrin, hesperidin, and pharmacologically acceptable salts thereof).

Examples of amino acids include leucine, isoleucine, valine, methionine, threonine, alanine, phenylalanine, tryptophan, lysine, glycine, asparagine, aspartic acid, serine, glutamine, glutamic acid, proline, tyrosine, cysteine, histidine, ornithine, hydroxyproline, hydroxylysine, glycylglycine, aminoethylsulfonic acid (taurine), cystine, or pharmacologically acceptable salts thereof.

The alcoholic injury mitigating agent and alcohol metabolism promoting agent of the present invention may be prepared in a suitable form for pharmaceutical compositions, functional foods, health foods, supplements, and others, for example, in the form of various solid pharmaceutical drugs such as granules (including dry syrups), capsules (soft capsules, hard capsules), tablets (including chewable tablets), powders, or pills, or liquid pharmaceutical drugs such as liquid drugs for internal use (including liquids, suspensions, syrups).

Additives to be used for producing a pharmaceutical preparation include, but are not limited to, vehicles, lubricants, binders, disintegrators, plasticizers, dispersants, wetting agents, antiseptics, thickening agents, pH adjustors, coloring agents, corrigents, surfactants, and solubilizers. When preparing the inventive agent in the form of a liquid drug, a thickening agent such as pectin, xanthan gum, or guar gum can be added. The inventive agent can be made into a coated tablet using a coating agent or made into paste glue. The inventive agent can be prepared in any other forms according to conventional preparation methods.

Further, the composition of the present invention can be added to any foods and beverages that can be mixed with fats and oils. For example, the inventive composition can be used as an additive for various beverages and foods such as confectioneries, bread, and soup. The composition is preferably added to, for example, drinks that are light and easy to drink before alcohol consumption, confectionaries such as chewable tablets, and snack foods to go with alcohol. The processes for producing such foods and beverages are not particularly limited as long as the effects of the invention are impaired: in other words, they can be produced according to any processes that are commonly used by those skilled in the art in respective applications. The inventive composition may be used in combination with components that are generally used to prevent drunkenness, such as fish and shellfish (e.g., *Cyrenidae*) extracts containing taurine or the like, or turmeric extracts containing curcumin or the like. Alternatively, the composition can be used with taurine or curcumin

EXAMPLES

The present invention will be specifically described by way of Examples given below, but the scope of the present invention is not limited thereto.

Example 1

Preparation of Krill Oil

The krill oil can be prepared by any procedures as typically disclosed in WO 2010/035749 A1 and WO 2010/035750 A1. The specific preparation example is described below.

Fresh Antarctic krill (10 t) just after being caught was squeezed using a meat separator (BAADER; Model: BAADER 605) to give a squeezed liquid (3 t). The resulting squeezed liquid (800 kg) was put in a stainless tank and heated by applying steam at 140° C. directly to it. The heating was stopped after the temperature of the squeezed liquid was confirmed to reach 85° C. at the end of the heating for about 60 minutes. The valve on the bottom of the tank was opened to remove liquid components that were able to pass through openings of 2 mm mesh by allowing them to drop under gravity, and the solids (heat-coagulated product) remaining on the mesh were washed by showering them with the same amount (3 t) of water. Then, the heat-coagulated product was put in aluminum trays at a rate of 12 kg per tray and was flash-frozen in a contact freezer.

The resulting frozen heat-coagulated product (1 t) was put in water (3,000 L), heated with stirring to 65° C., and kept for 10 minutes. After being drained using a 24-msh nylon screen, the solids were put again in water (3,000 L, 20° C.). After being stirred for 15 minutes, the suspension was drained using a 24-mesh nylon screen and treated using a centrifuge (Centrifugal Separator O-30 manufactured by Tanabe Willtec Inc.) for 15 seconds to give the solids (564 kg, 73% moisture). Tocopherol (1.54 kg) was added to the resulting solids, and they were mixed well with a mixer and dried in hot air at 60° C. for 3.2 hours to give a dry product (148.4 kg).

Then, 99% (v/v) ethanol (1,200 L) was added to the resulting dry product (299.6 kg), and the mixture was heated to 60° C. and stirred for 2 hours. After the stirring, the mixture was passed through a 100-mesh nylon screen to separate it into the solid and liquid phases by allowing it to drop under gravity, whereby extract A and extraction sediments a) were obtained. 99% (v/v) ethanol (800 L) was added to extracted sediments a), and the mixture was heated to 60° C. and stirred for 2 hours. After the stirring, the mixture was separated into the solid and liquid phases using a 100-mesh nylon screen to give extract B and extracted sediments b). 99% (v/v) ethanol (700 L) was added to extracted sediments b), and the mixture was heated to 60° C. and stirred for 2 hours. After the stirring, the mixture was passed through a 100-mesh nylon screen to separate it into the solid and liquid phases, whereby extract C and extracted sediments c) (390 kg) (the weight was reduced to 61.8% after drying at 105° C. for 4 hours) were obtained. Extracts A, B, and C were mixed into one (2,089 kg), and the mixture was concentrated under reduced pressure at a liquid temperature of 60° C. or lower to distill off ethanol and water, whereby an extract (141.6 kg) was yielded. The resulting extract was used as kill oil in the study that follows.

The results of the analysis of the krill oil for phospholipids content, astaxanthin content, and fatty acids composition are shown in Tables 1 and 2.

TABLE 1

| Component | Unit | Measured value |
|---|---|---|
| Phospholipids | (%) | 47.2 |
| Astaxanthin | (ppm) | 188 |

TABLE 2

| Fatty acid | Fatty acid composition (%) |
|---|---|
| C14:0 | 10.9 |
| C16:0 | 20.3 |
| C18:1 | 17.1 |
| C18:2 | 1.6 |
| C18:3 | 1.6 |
| C18:4 | 2.8 |
| 20:5 (EPA) | 15.0 |
| 22:6 (DHA) | 7.3 |

Example 2

Administration of the Krill Oil to Test Animals (1) Preparation of a Test Substance The krill oil to be orally administered was prepared as described below and stored in a brown glass bottle until use. The control group was administered only the same amount of olive oil.

Test substance for use to administer 200 mg of krill oil: Prepared by suspending the krill oil in olive oil using a pestle and mortar such that 200 mg of the krill oil was contained in a 3 mL suspension.

Test substance for use to administer 1000 mg of krill oil: Prepared by suspending the krill oil in olive oil using a pestle and mortar such that 1000 mg of the krill oil was contained in a 3 mL suspension.

(2) Preparation of a 60% (v/v) Ethanol Solution

The solution was prepared by mixing ethanol (purity 99.5%, Wako Pure Chemical Industries, Ltd.) and water for injection (Otsuka Pharmaceutical Factory, Inc.) at a ratio of 60.3:39.7 and stored in a brown glass bottle at room temperature.

(3) Administration of the Test Substance and the 60% (v/v) Ethanol Solution

Figure 1:
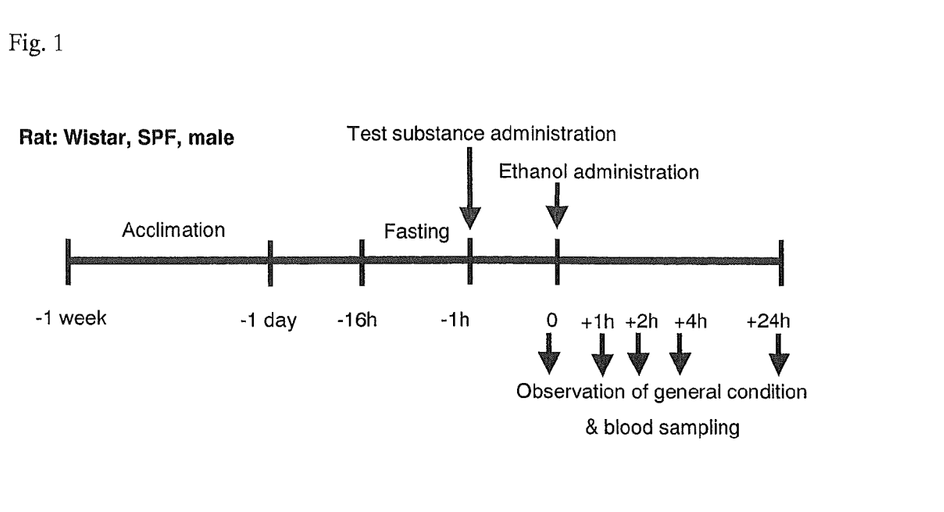
FIG. 1 shows the schedule of the administrations of the test substance and alcohol performed in Example 1. Rats were used as test animals and a 60% (v/v) ethanol solution was administered as alcohol.

The test substance and the 60% (v/v) ethanol solution were administered to rats according to the schedule shown in FIG. 1. Unless otherwise specified, the rats were bred under the following conditions:
Temperature: 20-26° C.;
Relative humidity: 40-70%;
Ventilation frequency: 10-20 times/hour;
Lighting time: 12 hours (7:00-19:00);
Feed: Voluntary intake of fish meal-free powdered feed (FR-1, Funabashi Farm Co. Ltd.);
Drinking water: Voluntary intake of tap water from a water bottle.

Eight-week-old male Wister rats were purchased (from Japan SLC, Inc.), and were quarantined and acclimated for 6 days. Those rats which were observed to have grown well and healthy in this period judging from the general condition and body weight were selected and used as test animals. The selected rats were divided into four groups (A1 to A4), each consisting of 12 rats, such that all groups had the same average body weight. The detailed information of the respective groups is shown in Table 3.

TABLE 3

| Group | Test substance | Active ingredient dose (mg/kg) | administered liquid volume (mL/kg) | 60% (v/v) ethanol volume (mL/kg) | Number of rats |
|---|---|---|---|---|---|
| A1 | Untreated | — | — | — | 12 |
| A2 | Olive oil | — | 3 | 12 | 12 |
| A3 | Krill oil | 200 | 3 | 12 | 12 |
| A4 | Krill oil | 1,000 | 3 | 12 | 12 |

The rats were fasted from one hour to 16 hours before receiving the 60% (v/v) ethanol solution. Then, they were forced to take the test substance orally once using a disposable oral feeding needle and syringe. One hour after the administration of the test substance, the 60% (v/v) ethanol solution was administered. The doses of the test substance and the 60% (v/v) ethanol solution were calculated on the basis of the body weight of each animal measured on the day of administration.

Observation of general condition and blood sampling were made before and 1, 2, 4, and 24 hours after the administration of the 60% (v/v) ethanol solution.

(4) Measurement of Blood Ethanol Concentration

Figure 2:
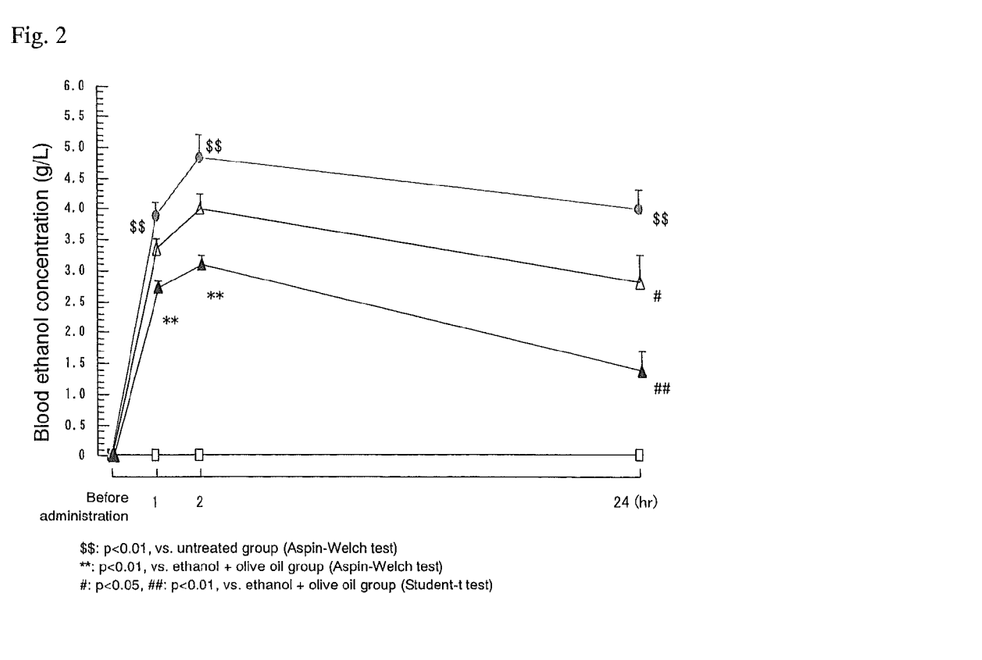
FIG. 2 shows the changes in blood ethanol concentration in the rats according to Example 2. □: Untreated group (A1), ●: 60% (v/v) ethanol+olive oil group (A2), Δ: 60% (v/v) ethanol+krill oil (200 mg/kg) group (A3), and ▲: 60% (v/v) ethanol+krill oil (1,000 mg/kg) group (A4). The data in the figure are expressed as averages. $$ represents $p<0.01$, vs. untreated group (Aspin-Welch test); ** represents $p<0.01$, vs. ethanol+olive oil group (Aspin-Welch test); # represents $p<0.05$, vs. ethanol+olive oil group (Student-t test); and ## represents $p<0.01$, vs. ethanol+olive oil group (Student-t test).

Heparin was added to the blood samples drawn before and 1, 2, and 24 hours after the administration of the 60% (v/v) ethanol solution, the samples were measured for blood ethanol concentration, and the average value of this parameter was calculated for each group (FIG. 2).

All the test groups except the untreated group (A1) showed an increase in blood ethanol concentration after the administration of the 60% (v/v) ethanol solution, but the increase in blood ethanol concentration was smaller in the krill oil-treated groups (A3 and A4) than in the olive oil-treated group (A2). This effect was more prominent 24 hours after the administration of the ethanol solution. The results demonstrate that consumption of the krill oil promotes alcohol metabolism in a dose-dependent manner.

(5) Observation of the General Condition of the Rats

Figure 3:
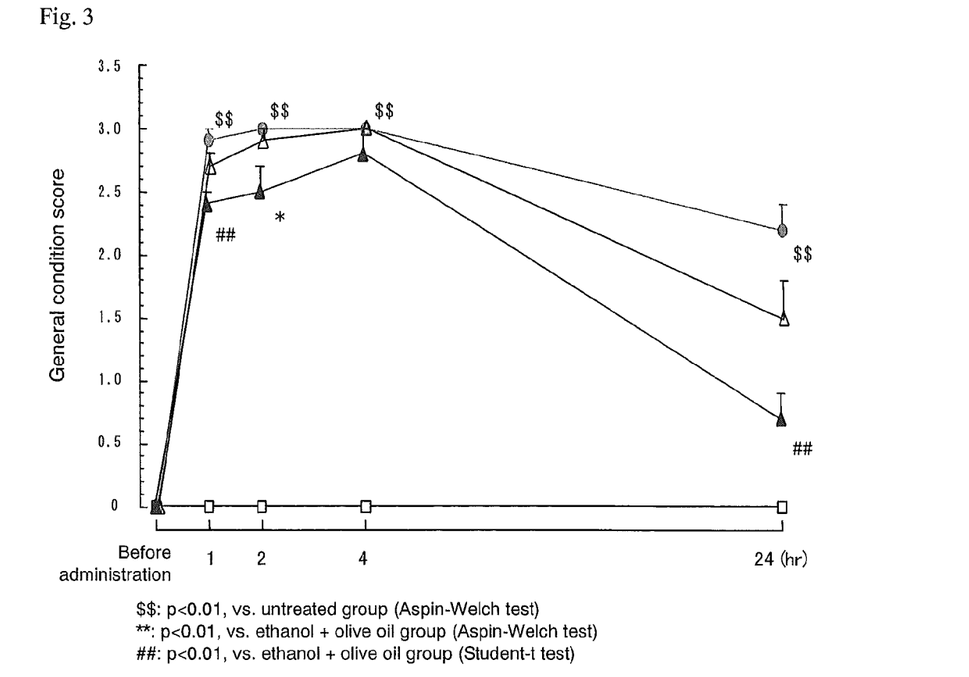
FIG. 3 shows the results of observation of general condition in the rats after ethanol administration in Example 2. The general condition score, which is based on walking state and righting reflex, reflects the state of drunkenness. □: Untreated group (A1), ●: 60% (v/v) ethanol+olive oil group (A2), Δ: 60% (v/v) ethanol+krill oil (200 mg/kg) group (A3), and ▲: 60% (v/v) ethanol+krill oil (1,000 mg/kg) group (A4). The data in the figure are expressed as averages. $$ represents $p<0.01$, vs. untreated group (Aspin-Welch test); ** represents $p<0.01$, vs. ethanol+olive oil group (Aspin-Welch test); and ## represents $p<0.01$, vs. ethanol+olive oil group (Student-t test).

The rats were observed for general condition before and 1, 2, 4, and 24 hours after the administration of the ethanol solution (FIG. 3). From one hour after the ethanol administration, all the test groups except the untreated group (A1) which received no 60% (v/v) ethanol solution (A2 to A4) were observed to be drunk due to the ethanol administration—more specifically, slightly drunk, inebriated, somnolent, dead drunk, or comatose. Among them, the krill oil (1,000 mg/kg)-treated group (A4) experienced significantly suppressed drunkenness as compared with the olive oil-treated group, and this effect was more prominent 24 hours after the administration of the 60% (v/v) ethanol solution.

From 4 to 24 hours after the administration of the 60% (v/v) ethanol solution, 2 rats each in the olive oil-treated group (A2) and the krill oil (200 mg/kg)-treated group (A3) died, possibly due to acute alcoholism caused by consumption of large amounts of alcohol. In contrast, no rat in the krill oil (1,000 mg/kg)-treated group (A4) died after the ethanol administration.

(6) Measurement of Hematocrit (HCT)

Figure 4:
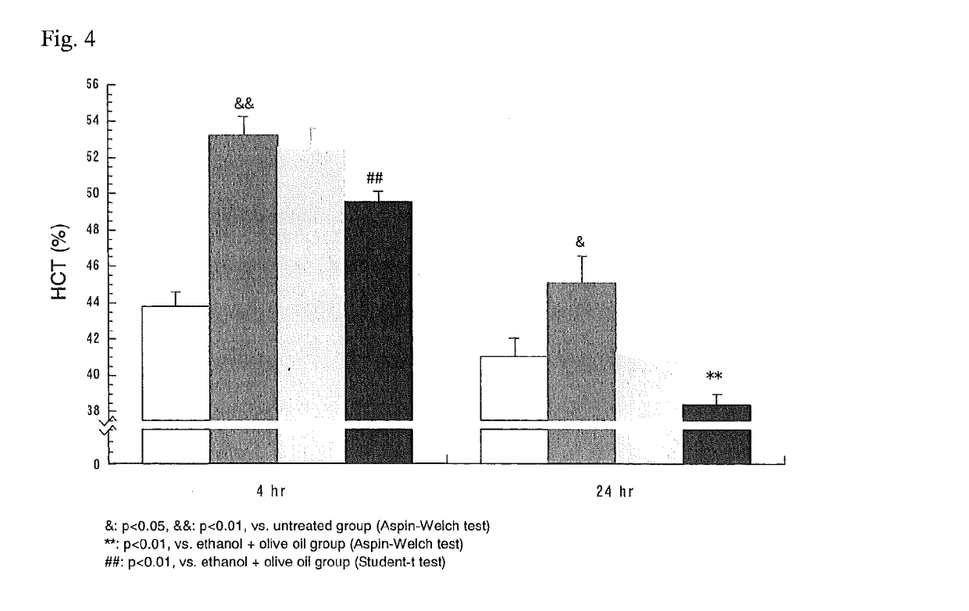

EDTA-2K was added to the blood samples drawn before and 4 and 24 hours after the administration of the 60% (v/v) ethanol solution, and the samples were used for HCT measurement (FIG. 4).

The olive oil-treated group (A2) showed an increase in HCT as compared with the untreated group (A1). The krill oil (200 mg/kg)-treated group (A3) displayed no significant difference in HCT compared with the olive oil-treated group (A2) at the time of 4 hours after the ethanol administration but showed a significant decrease in HCT at the time of 24 hours after the ethanol administration. The increase in HCT was more remarkably suppressed in the krill oil (1,000 mg/kg)-treated group (A4). The results demonstrate that the krill oil suppresses dehydration in a dose-dependent manner.

(7) Measurement of Blood Aspartate Aminotransferase (AST) Activity

Figure 5:
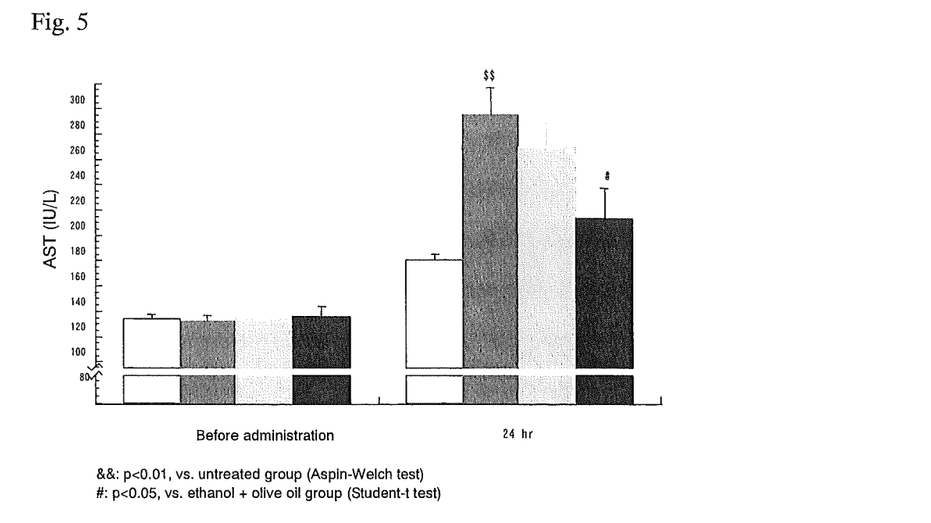

Heparin was added to the blood samples drawn before and 24 hours after the administration of the 60% (v/v) ethanol solution, and the samples were centrifuged at 1700×g at 4° C. for 15 minutes to obtain plasma samples. The resulting plasma samples were used for AST activity measurement (FIG. 5).

All the groups (A2 to A4) which received the 60% (v/v) ethanol solution showed an increase in AST activity. The AST activity after the ethanol administration was more suppressed in the krill oil-treated groups (A3 and A4) than in the olive oil-treated group (A2). In particular, this activity was remarkably suppressed by the administration of 1,000 mg/kg of the krill oil (A4).

(8) Measurement of Blood Alanine Aminotransferase (ALT) Activity

Figure 6:
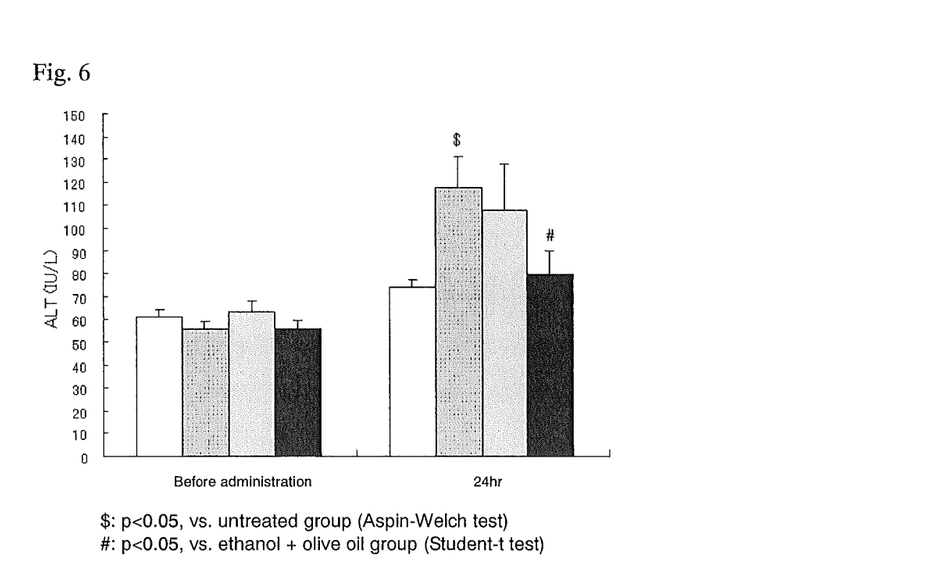

Heparin was added to the blood samples drawn before and 24 hours after the administration of the 60% (v/v) ethanol solution, and the samples were centrifuged at 1700×g at 4° C. for 15 minutes to obtain plasma samples. The resulting plasma samples were used for ALT activity measurement (FIG. 6).

All the groups (A2 to A4) which received the 60% (v/v) ethanol solution showed an increase in ALT activity. The ALT activity after the ethanol administration was more suppressed in the krill oil-treated groups (A3 and A4) than in the olive oil-treated group (A2). In particular, this activity was remarkably suppressed by the administration of 1,000 mg/kg of the krill oil (A4).

(9) Measurement of Blood Glucose Level

Figure 7:
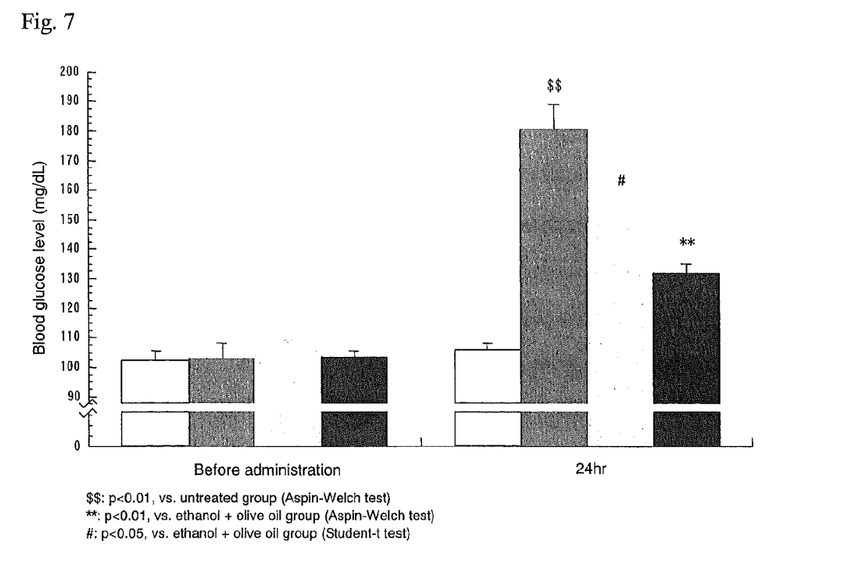

Heparin was added to the blood samples drawn before and 24 hours after the administration of the 60% (v/v) ethanol solution, and the samples were centrifuged at 1700×g at 4° C. for 15 minutes to obtain plasma samples. The resulting plasma samples were used for measuring glucose level (FIG. 7).

After the administration of the 60% (v/v) ethanol solution, all the treated groups (A2 to A4) showed an increase in blood glucose level. As compared with the untreated group (A1), the olive oil-treated group (A2) had a higher blood glucose level even 24 hours after the administration of the ethanol solution. In the krill oil-treated groups (A3 and A4), the increase in blood glucose level was suppressed in a dose-dependent manner.

Example 3

Effects of the Krill Oil on Alcohol Consumption in Humans

The effects of the krill oil on alcohol consumption in humans were studied by measuring their breath ethanol concentration and breath acetaldehyde concentration after alcohol consumption.

(1) Preparation of Test Foods

Soft capsules each containing the krill oil prepared in Example 1 or refined olive oil in an amount of 250 mg were prepared. Both types of soft capsules used were colored so that their content could not be distinguished by their appearance.

(2) Subjects

Five healthy male subjects aged 40 or older.

(3) Test Method

A double blind crossover study using olive oil as the control was carried out. A 2-week washout period was scheduled.

The subjects were prohibited from drinking alcohol since the day before the study, and were instructed to have a lunch of the uniform menu (boxed lunch with fried chicken) between 12:00 and 13:00 on the day of the study. After the lunch, they were prohibited from having anything but water. The study began at 16:00.

Thirty minutes before alcohol consumption, the subjects were instructed to taken 8 soft capsules containing the krill oil or olive oil (2 g of the krill oil or olive oil, at a dose of 23-34 mg per kg body weight of the subject). They consumed alcohol by drinking barley shochu with an alcohol content of 25%. The alcohol intake was adjusted based on the body weight of each subject so as to give a net alcohol intake of 0.5 g per kg body weight. The subjects were instructed to consume the adjusted dose of barley shochu over 10 minutes. After the beginning of the drinking, they were only allowed to drink enough water to quench their thirst.

They underwent sampling of breath 30, 60, 90, 120 and 150 minutes after the drinking. Expired air was sampled by inhaling air from their nose, holding their breath for 10 seconds, and then breathing into a zip-up plastic bag (280×200×0.04 mm) so as to fill it with their breaths. The breath samples were subjected to the measurement of ethanol concentration using a detector (Gastec Corporation, GV-100S) and an ethanol detector tube (Gastec Corporation, No. 92L) connected thereto, and also to the measurement of acetaldehyde concentration using a detector (Gastec Corporation, GV-100S) and an acetaldehyde detector tube (Gastec Corporation, No. 92L) connected thereto.

(4) Results

Figure 8:
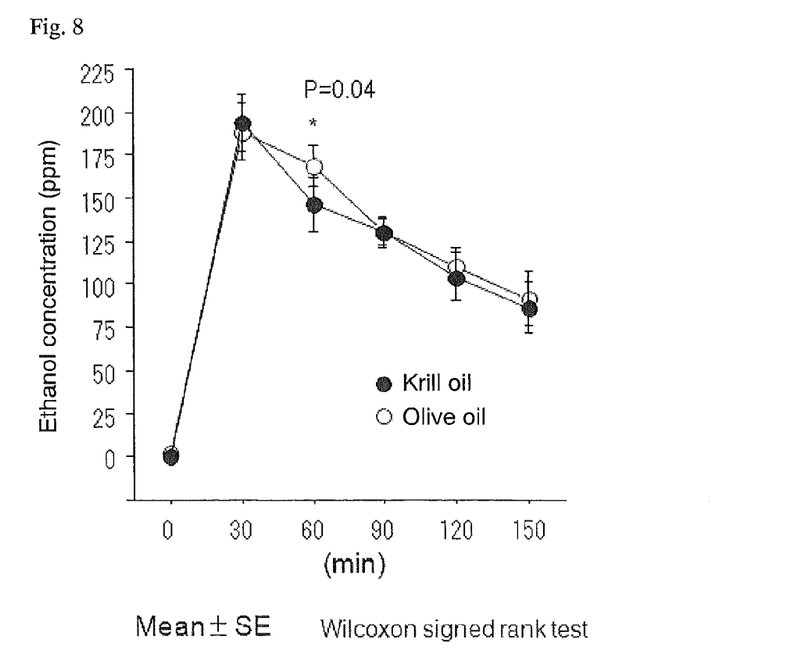
FIG. 8 shows the changes with time in breath ethanol concentration according to Example 3. The horizontal axis represents time after alcohol consumption (in min). ●: Krill oil consumption, and ○: Olive oil consumption. The data in the figure are expressed as the averages (Mean±SE) of the ethanol concentrations in the breath samples from 5 subjects. * represents $p=0.04$, vs. olive oil (Wilcoxon signed rank test).

Ethanol was detected in all of the breath samples collected from the subjects (5 persons). FIG. 8 shows the changes with time in ethanol concentration in the breath samples. The ethanol concentrations shown in this figure are expressed as the averages of the ethanol concentrations in the breath samples from the subjects (5 persons). In the breath samples collected 30 minutes after the alcohol consumption, the highest ethanol concentration was detected but there was no significant difference in ethanol concentration between the case where the subjects received the krill oil and the case where they received olive oil. However, in the breath samples collected 60 minutes after the alcohol consumption, a significant decrease in ethanol concentration was observed in the case where they received the krill oil as compared with the case where they received olive oil ($p=0.04$, Wilcoxon signed rank test).

Figure 9:
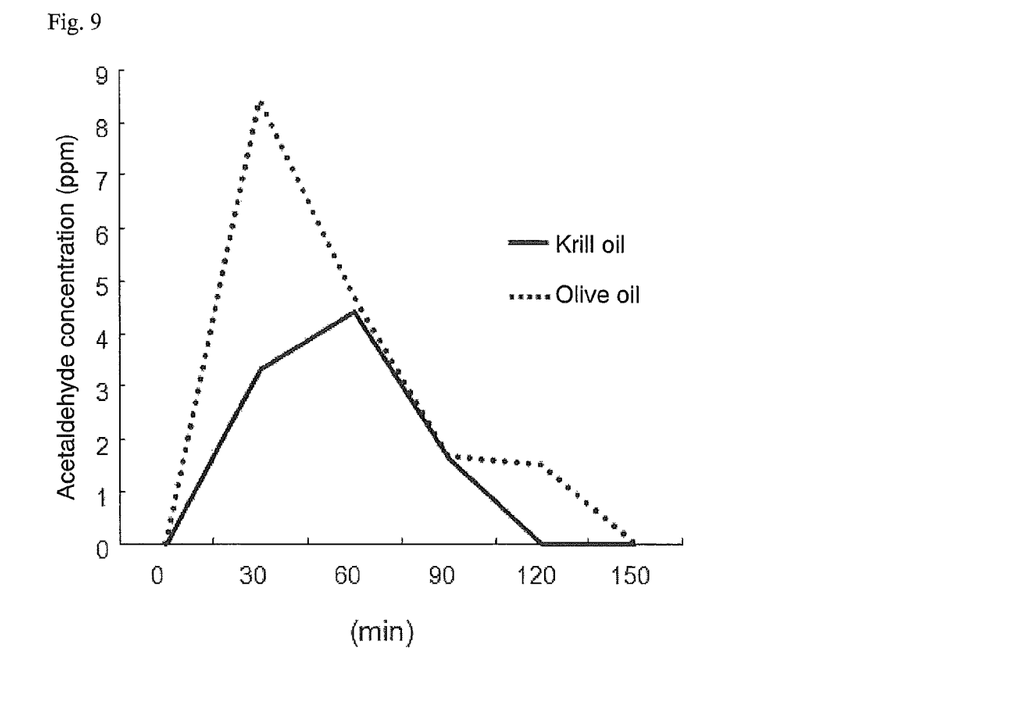
FIG. 9 shows the changes with time in breath acetaldehyde concentration according to Example 3. The horizontal axis represents time after alcohol consumption (in min). Solid line: Krill oil consumption, and dotted line: Olive oil consumption.

Acetaldehyde was only detected in the breath sample collected from one of the subjects (5 persons); the concentrations detected in the samples from the other 4 subjects were below the limit of detection. FIG. 9 shows the changes with time in acetaldehyde concentration in the breath samples collected from that subject. The breath acetaldehyde concentration was found to be remarkably lower in the case where he received the krill oil than in the case where he received olive oil. Also, in the case where he received the krill oil, the breath acetaldehyde concentration decreased to below the limit of detection at the time of 120 minutes after the alcohol consumption.

The results presented above demonstrate that consumption of the krill oil promotes alcohol metabolism and suppresses an increase in the concentration of acetaldehyde which is responsible for uncomfortable feeling and organopathy such as alcoholic liver injury induced by alcohol consumption.

Example 4

Comparison with Soybean Lecithin and Refined Fish Oil

The breath acetaldehyde concentration was selected as an indicator that would show easily detectable differences, and the effects of soybean lecithin and refined fish oil were confirmed in the subject who had acetaldehyde detected in his breath in Example 3 for comparison.

(1) Preparation of Test Foods

The additional oils used were commercially available refined fish oil (28 wt. % EPA and 12 wt. % DHA of total fatty acids) and soybean lecithin (60 wt. % phospholipids). Soft capsules each containing refined fish oil or soybean lecithin in an amount of 250 mg were prepared as in Example 3.

(2) Subject

Fifty-year-old healthy male subject (weight 65 kg) in whose breath acetaldehyde was detected in Example 3.

(3) Test Method

Following the same procedure as in Example 3, soft capsules containing refined fish oil and soybean lecithin were administered to the subject, breath samples were collected from him, and the samples were subjected to the measurement of acetaldehyde concentration.

(4) Results

Figure 10:
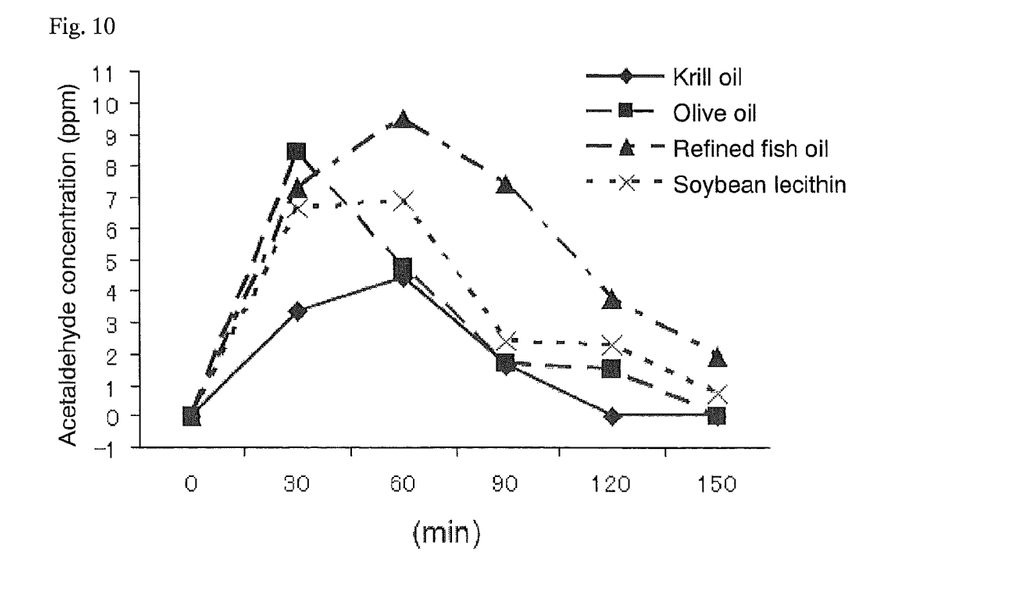
FIG. 10 shows the changes with time in breath acetaldehyde concentration according to Example 4 along with the results obtained in Example 3. The horizontal axis represents time after alcohol consumption (in min) ◆: Krill oil consumption, ■: Olive oil consumption, ▲: Refined fish oil consumption, and x: Soybean lecithin consumption.

FIG. 10 shows the changes with time in breath acetaldehyde concentration along with the results obtained in FIG. 9. The breath acetaldehyde concentration was found to be remarkably lower in the case where he received the krill oil than where he received olive oil, refined fish oil, or soybean lecithin.

Also, in the case where he received the krill oil, the breath acetaldehyde concentration decreased to below the limit of detection at the time of 120 minutes after the alcohol consumption. However, in the cases where he received olive oil, refined fish oil, or soybean lecithin, this concentration decreased to below the limit of detection at the time of 150 minutes or later after the alcohol consumption.

The results presented above demonstrate that consumption of the krill oil promotes alcohol metabolism and suppresses an increase in the concentration of acetaldehyde which is responsible for uncomfortable feeling and organopathy such as alcoholic liver injury induced by alcohol consumption. The results also demonstrate that the effects of the krill oil are remarkably higher than those of refined fish oil, soybean lecithin, and the like.

The Examples given above demonstrate the following. Namely, the rats administered alcohol developed typical symptoms caused by alcohol consumption such as change in apparent mobility (drunkenness), dehydration, increase in blood glucose level, increase in blood ALT activity, and increase in blood AST activity. The krill oil, which is capable of reducing the alcohol concentration in the body, reduced these symptoms and helped the rats to recover faster from the symptoms to their normal state. These effects were also observed in humans, but no comparable effect could not be produced by the consumption of either refined fish oil which is a triglyceride containing EPA and DHA or soybean lecithin comprising phospholipids as a major component. These findings demonstrate that the effects of the present invention are based on the characteristic effects of the krill oil which comprises phospholipids containing EPA and DHA.

The invention claimed is:

1. A method of treating alcoholic injury in a human after consumption of an alcoholic beverage consisting essentially of administering therapeutically effective amounts of krill oil to said human to treat alcoholic injury in the human.

2. A method according to claim 1, wherein treating said alcoholic injury is selected from the group consisting of suppression of an increase in blood ethanol concentration in the human, mitigation of a symptom of drunkenness in the human, promotion of recovery from the symptoms of drunkenness in the human, suppression of liver injury in the human, suppression of dehydration in the human, and suppression of an increase in blood glucose level in the human.

3. A method according to claim 1, wherein treating said alcoholic injury in the human is inhibition of alcohol absorption and/or promotion of alcohol metabolism in the human.

4. A method according to claim 1, wherein the krill oil contains phospholipids in an amount of at least 25% by weight.

5. A method according to claim 1, wherein at least 5% by weight of the total fatty acids in the krill oil is ω3 polyunsaturated fatty acids.

6. A method according to claim 1, wherein at least 2% by weight of the total fatty acids in the krill oil is eicosapentaenoic acid.

7. A method according to claim 1, wherein at least 1% by weight of the total fatty acids in the krill oil is docosahexaenoic acid.

8. A method according to claim 1, wherein the krill oil is administered daily in an amount in the range of 1 to 20000 mg.

* * * * *